United States Patent [19]
Pohndorf et al.

[11] Patent Number: 5,904,683
[45] Date of Patent: May 18, 1999

[54] ANTERIOR CERVICAL VERTEBRAL STABILIZING DEVICE

[75] Inventors: Peter J. Pohndorf, Stillwater; Richard A. Erickson, Edina, both of Minn.

[73] Assignee: Sulzer Spine-Tech Inc., Minneapolis, Mich.

[21] Appl. No.: 09/113,886

[22] Filed: Jul. 10, 1998

[51] Int. Cl.⁶ .................................................. A61B 17/58
[52] U.S. Cl. ................................. 606/61; 606/69; 606/73
[58] Field of Search .............................. 606/60, 61, 69, 606/70, 71, 72, 73

[56] References Cited

U.S. PATENT DOCUMENTS

| | | | |
|---|---|---|---|
| 5,300,074 | 4/1994 | Frigg | 606/69 |
| 5,676,666 | 10/1997 | Oxland et al. | 606/61 |
| 5,709,686 | 1/1998 | Talos et al. | 606/69 |
| 5,713,900 | 2/1998 | Benzel et al. | 606/61 |
| 5,810,822 | 9/1998 | Mortier | 606/69 |

*Primary Examiner*—Michael Buiz
*Assistant Examiner*—Daphna Shai
*Attorney, Agent, or Firm*—Kenneth S. Barrow

[57] ABSTRACT

An implantable device for affixing to the anterior side of cervical vertebrae for stabilizing the cervical vertebral column. A plate has an anterior surface and a posterior surface and a plurality of through holes open at the anterior surface and at the posterior surface. Each hole has an anterior portion having a first diameter and a posterior portion having a second diameter. The second diameter is smaller than the first diameter, and the anterior portion of the hole is internally threaded. A bone screw has a threaded shank having a major diameter smaller than the second diameter of the through hole of the plate. The bone screw also has a head having a major diameter greater than the second diameter of the through hole of the plate and smaller than the first diameter of the hole of the plate. A locking cap has an exterior thread and is sized to be threadedly received within the anterior portion of the through hole of the plate while the head of the bone screw is disposed within the through hole. The locking cap is provided for engaging and frictionally locking the head of the bone screw to the plate.

15 Claims, 5 Drawing Sheets

ANTERIOR CERVICAL VERTEBRAL STABILIZING DEVICE

BACKGROUND OF THE INVENTION

1. Field of the Invention

The invention relates generally to implantable medical devices and their methods of use for stabilizing skeletal bone, and relates more particularly to implantable medical devices and their methods of use for stabilizing the cervical vertebrae of a human spine.

2. Background of the Related Art

In humans, the spine is adapted to function as the central column of the skeleton, thereby permitting the erect posture that is characteristic of humankind. The human vertebral column includes adjacent sections of vertebrae that form curves of opposite sense in the sagittal plane. The central, or thoracic, section of the vertebral column is convex posteriorly, whereas the lumbar (lower back) and cervical (neck) sections of the vertebral column are concave posteriorly. The posteriorly concave curvature of the cervical and lumbar vertebral columns is known as lordosis.

The cervical vertebral column, with which the present invention is particularly concerned, includes seven stacked vertebrae making up two anatomically and functionally distinct segments. The superior, or suboccipital, segment contains the first vertebrae, the atlas, immediately adjacent the occiput of the skull, and a second vertebrae, known as the axis. The inferior segment contains five vertebrae that link the inferior surface of the axis to the superior surface of the first thoracic vertebrae. The atlas and the axis are each uniquely shaped, and are connected to each other and to the occiput to permit three degrees of freedom. The vertebrae of the inferior segment, in contrast, are all alike and are restricted to certain movements: flexion and extension in the sagittal plane, and lateral flexion with rotation.

In healthy individuals with normal anatomy, the vertebrae of the cervical column are held together and to the remainder of the skeleton by a complex arrangement of ligaments, tendons and muscles, resulting in a columnar frame that is significantly plastic, yet stabile and capable of rigidity. The cervical vertebrae play another very important role as a mechanical protector of the neuraxis, or spinal cord. Consequently, any loss of stability of the cervical vertebrae can present a serious threat to the integrity of the neuraxis, and thus to the life, mobility and health of the individual. Trauma or degenerative disease can result in a loss of stability of cervical vertebrae that requires surgical intervention. In some cases, implantation of stabilizing plates using bone screws to link adjacent vertebrae together may be indicated.

In the past, a posterior surgical approach was often used to implant plates or braces to stabilize the cervical spine. Beginning in the 1950's an anterior approach was developed. The anterior approach increased in popularity over the years and began to eclipse the posterior approach in the 1970's. In the anterior approach, the cervical plate spans and is affixed to adjacent cervical vertebrae on their anterior surfaces. The use of the anterior surgical approach and anterior cervical plating has certain advantages. These advantages include maintaining the patient in the supine position, requiring minimal tissue disruption for anatomic dissection, the ability to obtain anterior decompression of vertebrae, and exploiting an optimal environment for promoting bone fusion, i.e., bone under compression.

During early development of the technique of anterior cervical plating, surgeons used available bone plates and screws that had been developed for other bone stabilizing operations. W. Caspar developed the first plate and screw system specifically for use in the cervical spine. The Caspar plate could be contoured to reestablish the normal cervical lordosis. Some of the early anterior cervical plating systems involved a non-constrained arrangement in which bone screws, received through elongated holes or slots in the plate, were not rigidly affixed to the plate at their interface with the plate. This non-constrained arrangement permitted relative movement between the screw heads and the plate, which provided less stress shielding of the bone and allowed for subsidence. To prevent toggling and loosening of the bone screws, non-constrained cervical plating systems often required the bone screws to be implanted with bicortical purchase, in which the bone screw engaged the posterior cortical bone of the vertebrae in addition to passing through the anterior cortical bone.

Many surgeons were insecure with the use of bicortical purchase because of the risk of drilling through the posterior cortex and causing direct neural injury. As a consequence, constrained cervical plating systems using unicortical screw purchase gained in popularity. Concerns about screw loosening resulting in esophageal injury, as well as the need to secure the unicortical purchase screw against toggling, led to the development of mechanisms for locking the head of the screw to the plate. Such locking mechanisms prevented the screw from backing out of the plate and resisted any tendency of the screw to pivot relative to the plane of the plate. In some constrained anterior cervical plating systems, the relationship between the bone screw and the corresponding hole in the plate was such that the axis of the screw was fixed at a predetermined angle relative to the plate. To provide the surgeon with greater flexibility in placing the plate and in selecting the optimal orientation of the screw shaft, other constrained anterior cervical plating systems provided for multi-axial placement of the bone screw. Typically, in multi-axial systems, the bone screw can be placed at any angle up to about 10° to 20° from normal to the surface of the plate. After the plate is in place and the bone screws are installed and tightened at the selected angle, a locking mechanism is activated to maintain the screw at the selected angle.

Currently, the most desired characteristics of an anterior cervical plating system include the ability to use unicortical screw purchase, with the option to employ bicortical purchase, variability of the axis of screw placement in the superior, inferior, medial and lateral directions together with fixation of the screw to the plate, and titanium construction. Titanium is preferred because of its minimal interference with the magnetic resonant imaging (MRI) technique used for postoperative evaluation. Bendability or precurvature of the plate is also desired to accommodate or restore the natural lordosis of the cervical spine. These, and other desirable features and advantages, are provided by the present invention, particular embodiments of which are described below.

SUMMARY OF THE INVENTION

According to one aspect of the present invention, an implantable device is provided for affixing to the anterior side of cervical vertebrae for stablizing the cervical vertebral column. The device includes a plate having an anterior surface and a posterior surface. The plate has a plurality of through holes, each hole being open at the anterior surface and at the posterior surface. Each hole has an anterior portion having a first diameter and a posterior portion having a second diameter. The second diameter is smaller than the first diameter, and the anterior portion of the hole is internally threaded. A bone screw has a threaded shank having a major diameter smaller than the second diameter of the through hole of the plate. The bone screw also has a head having a major diameter greater than the second diameter of the through hole of the plate and smaller than the first diameter of the through hole of the plate. A locking cap has an exterior thread and is sized to be threadedly received within the anterior portion of the through hole of the plate while the head of the bone screw is disposed within the through hole. The locking cap is provided for engaging and frictionally locking the head of the bone screw to the plate.

It is an object of the present invention to provide an improved device for anterior stabilization of the cervical vertebral column. This and other objects and advantantages of the present invention will be apparent to those skilled in the pertinent art from the drawings and descriptions herein.

DETAILED DESCRIPTION OF THE PREFERRED EMBODIMENTS

Figure 1:
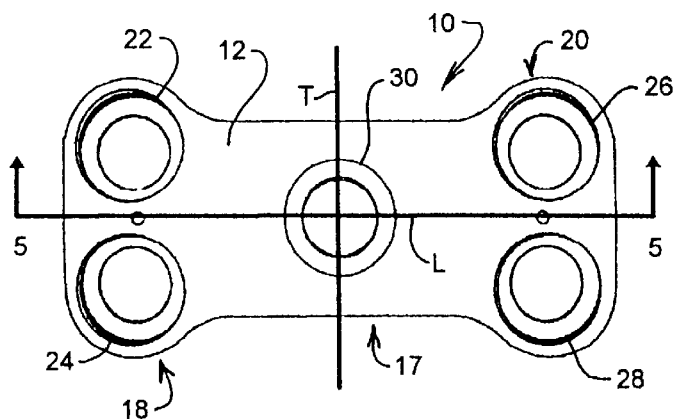
FIG. 1 is a plan view of an anterior cervical plate constructed in accordance with the present invention.
Figure 3:
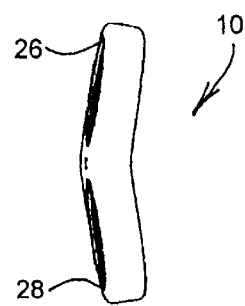
FIG. 3 is an end elevation view of the anterior cervical plate of FIG. 1.
Figure 2:
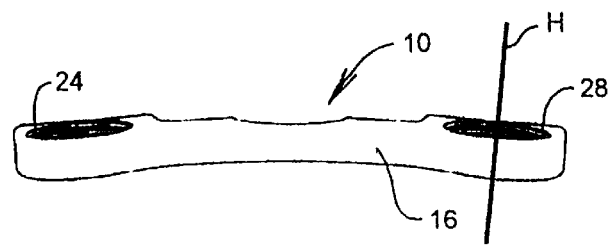
FIG. 2 is a side elevation view of the anterior cervical plate of FIG. 1.
Figure 4:
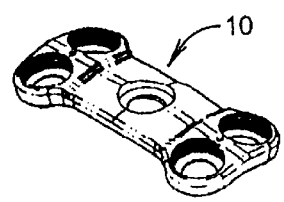
FIG. 4 is a perspective view of the anterior cervical plate of FIG. 1.

Referring to FIGS. 1–6, an anterior cervical plate 10 is shown constructed in accordance with the present invention. Plate 10 is constructed of a biocompatible material suitable for long term implantation in a human in proximity to the anterior surfaces of the cervical vertebrae. The preferred material is titanium, or a titanium alloy, to minimize interference with magnetic resonance imaging techniques for post-operative evaluations. Plate 10 is generally planar in the sense that its length and width dimensions significantly exceed its thickness dimensions, but it is not necessarily flat. In general, plate 10 has an anterior surface 12, a posterior surface 14, and a perimetrical edge surface 16. As preferred, plate 10 is generally rectangular in the sense that its length along longitudinal axis L is greater than its width along transverse axis T. Furthermore, plate 10 as preferred is curved in a longitudinal plane that is perpendicular to anterior surface 12 and that includes longitudinal axis L. Likewise, plate 10 as preferred is curved in a transverse plane that is perpendicular to anterior surface 12 and that includes longitudinal axis T. The direction of curvature in both the longitudinal and transverse planes is preferred to be the same, such that posterior surface 14 of plate 10 is generally concave and anterior surface 12 is generally convex. The radius of curvature in the longitudinal plane is selected to match the desired lordosis of the section of the cervical vertebral column to which plate 10 is to be affixed. The radius of curvature in the transverse plane is selected to conform to the transverse curvature of the anterior surfaces of the cervical vertebrae. The two aforementioned radii of curvature are not necessarily identical, and are not necessarily simple arcs. The transverse curvature, in particular, may be in the form of a v-shaped bend, as illustrated in FIG. 3.

Plate 10 includes a central portion 17 and two opposite end portions 18 and 20. Central portion 17 is of generally uniform width and thickness in the direction along longitudinal axis L. End portions 18 and 20 are of greater width than central portion 17, and of somewhat greater thickness than central portion 17, resulting in a flattened "dogbone" configuration of plate 10. As preferred, the thickness of end portions 18 and 20 is about 2.5 mm, and the thickness of central portion 17 is about 2.0 mm. End portions 18 and 20 each include two through-holes 22 and 24, and 26 and 28, respectively, for receiving bone screws. Central portion 17 includes a centered through-hole 30 similar to screw holes 22, 24, 26 and 28, for receiving a screw to engage and stabilize a bone graft replacement for an intervertebral disc. Holes 22–30 are described further below with reference to FIG. 6.

Figure 5:
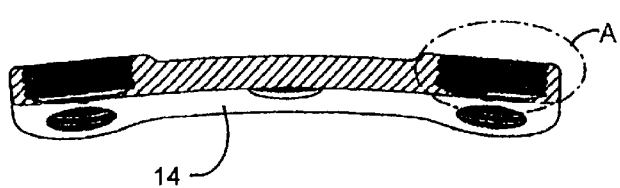
FIG. 5 is a cross-sectional view of the anterior cervical plate of FIG. 1, taken in plane 5—5 of FIG. 1 and viewed in the direction of the arrows.
Figure 6:
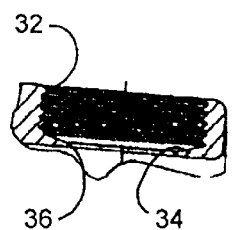
FIG. 6 is an enlarged cross-sectional view of area A of FIG. 1.
Figure 7:
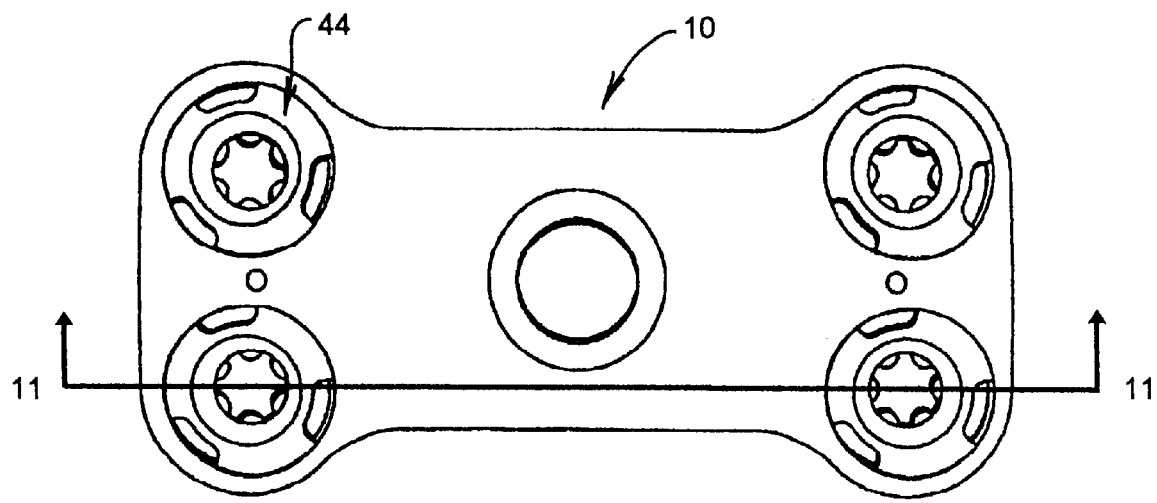
FIG. 7 is a plan view of the anterior cervical plate of FIG. 1, in which bone screws and retaining caps have been received.
Figure 8:
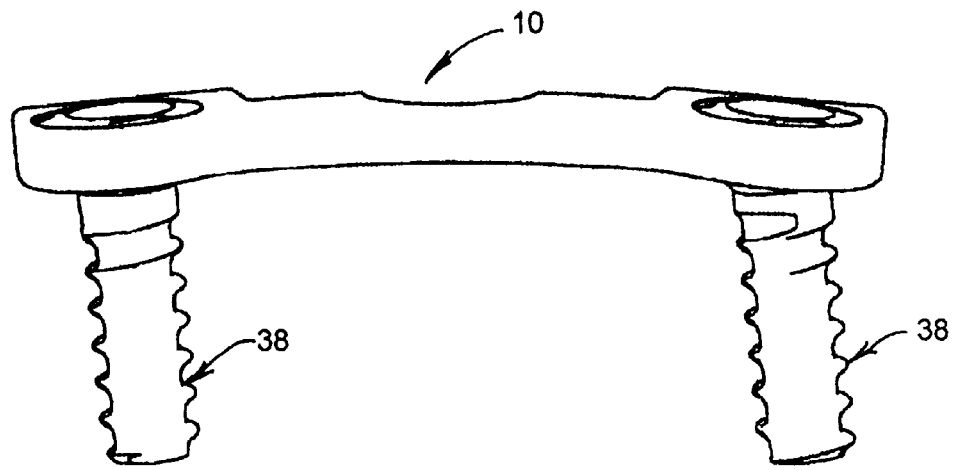
FIG. 8 is a side elevation view of the anterior cervical plate, bone screws and caps of FIG. 7.
Figure 9:
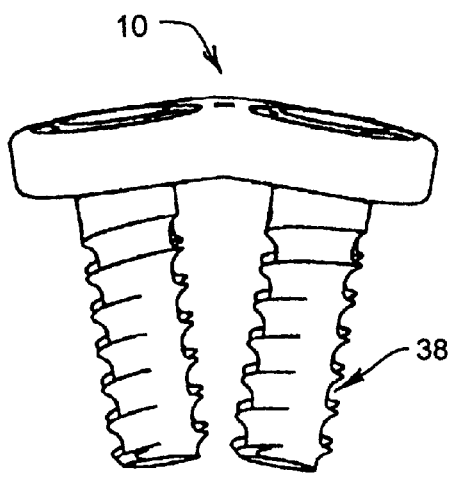
FIG. 9 is an end elevation view of the anterior cervical plate, bone screws and caps of FIG. 7.
Figure 10:
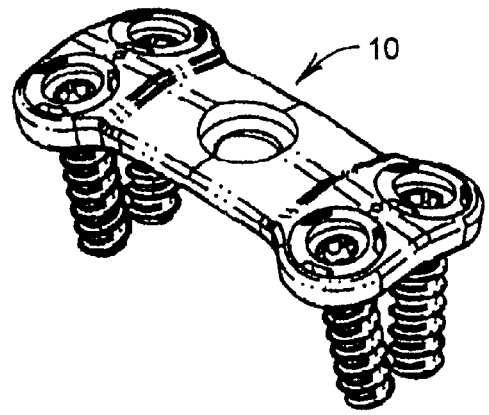
FIG. 10 is a perspective view of the anterior cervical plate, bone screws, and caps of FIG. 7.
Figure 11:
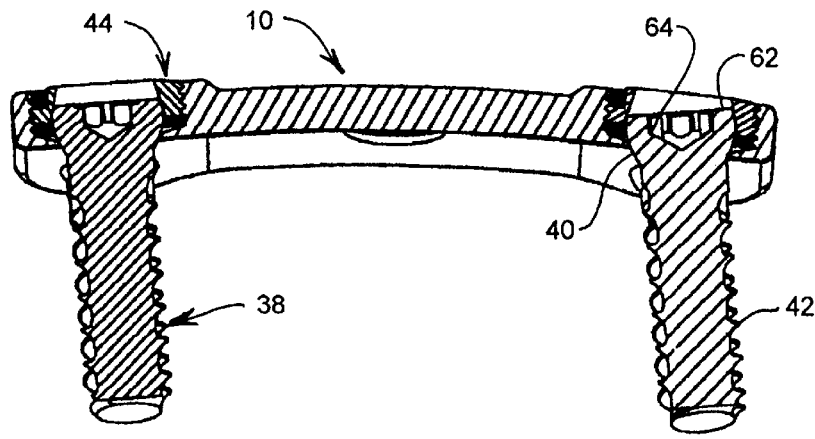
FIG. 11 is a cross-sectional view of the anterior cervical plate, bone screws and caps of FIG. 7, taken in plane 11—11 of FIG. 7 and viewed in the direction of the arrows.

Referring particularly to FIGS. 5 and 6, screw holes 22, 24, 26, 28 and 30 include a first cylindrical side wall 32, interiorly threaded, that extends to anterior surface 12. Screw holes 22, 24, 26, 28 and 30 are open anteriorly to the full extent of the diameter of first cylindrical side wall 32. First cylindrical side wall 32 terminates, in the posterior direction, at a juncture with a succeeding frusto-conical side wall 34 having a major diameter substantially equal to that of first cylindrical side wall 32 and tapering inwardly and posteriorly. Frusto-conical side wall 34 terminates, in the posterior direction, at a juncture with a succeeding second cylindrical side wall 36 having a diameter substantially equal to the minor diameter of frusto-conical side wall 34. Second cylindrical side wall 36 is non-threaded and extends to posterior surface 14. Consequently, screw holes 22, 24, 26, 28 and 30 are open posteriorly only to the extent of the minor diameter of frusto-conical side wall 34, which minor diameter is less than the diameter of first cylindrical side wall 32. The center axis of symmetry H of each screw hole 22, 24, 26, 28 and 30 is substantially normal to the anterior and posterior surfaces 12 and 14 at the respective site of the screw hole.

Referring to FIGS. 8, 9, 10 and 11, in particular, anterior cervical plate 10 is shown in combination with a plurality of bone screws 38, one of which is received in each of screw holes 22, 24, 26, 28 and 30. Bone screws 38 each include a head 40 and a threaded shaft 42. Head 40 has a major diameter that exceeds the major diameter of the threads of shaft 42. The undersurface of head 40, i.e., that part of head 40 adjacent threaded shaft 42, is substantially spherical in curvature. The major diameter of head 40 is smaller than the diameter of first cylindrical side wall 32 of the screw holes of plate 10, but greater than the minor diameter of frusto-conical side wall 34 of the screw holes of plate 10. Also, the major diameter of the threaded shaft 42 is smaller than the minor diameter of frusto-conical side wall 34 of the screw holes of plate 10. As a consequence, bone screws 38 can be inserted, shaft first, into any of screw holes 22, 24, 26 and 28 from the anterior side of plate 10, with the threaded shaft passing through the hole past the posterior surface 14. The spherical undersurface of head 40, however, having passed freely through that section of the screw hole defined by first cylindrical side wall 32, engages and bears against the frusto-conical side wall 34 of the screw hole. The relationship between the diameters of the threaded shaft 42, the head 40 and the side walls 32, 34 and 36 of the screw holes 22 et seq. is such that bone screw 38 can pivot, or toggle, while seated in the screw hole. The spherical undersurface of head 40 articulates against frusto-conical side wall 34 in a ball and socket arrangement. Consequently, the longitudinal axis of the shaft of bone screw 38 can be varied selectively as much as 10° from the center axis H of the screw hole, presenting the surgeon with polyaxial placement options for bone screw 38.

Figure 12:
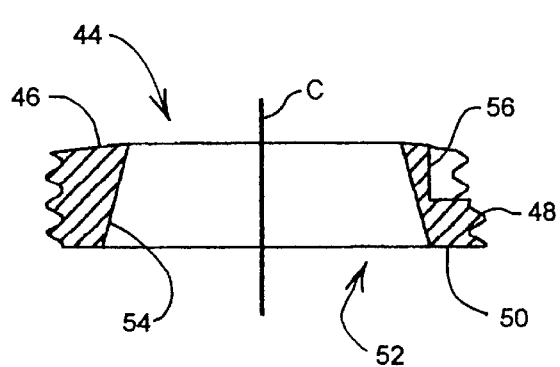
FIG. 12 is a cross-sectional view of the locking cap of FIG. 7.
Figure 13:
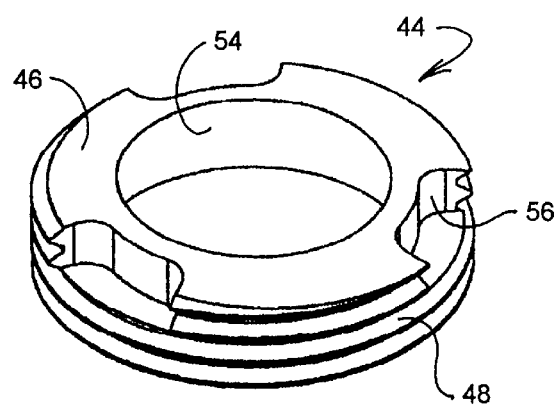
FIG. 13 is a perspective view of the locking cap of FIG. 12.

Once the optimum angular orientation for each bone screw 38 has been selected by the surgeon, other features of the invention permit the bone screw 38 to be locked to plate 10 in the selected orientation. Locking caps 44, enlarged views of which are shown in FIGS. 12 and 13, engage the plate 10 and the screw head 40 to lock the screw head against articulating relative to the plate after implantation. The locking effect is created by friction between the engaged surfaces, induced by pressure between the screw head and the plate and cap. The mutually engaging portions have been roughened by grit blasting to enhance the friction.

Figure 14:
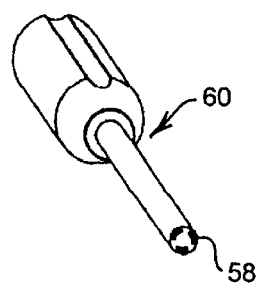
FIG. 14 is a a perspective view of a torque driver useful with the locking cap of FIG. 12.

Locking caps 44 are substantially disc shaped plugs, open in the center, having a slightly convex anterior surface 46, an exteriorly threaded cylindrical perimetrical side wall 48, and a substantially planar posterior surface 50. Communicating between the anterior surface 46 and the posterior surface 50 is a centrally located hole 52 defined by a frusto-conical side wall 54 that slopes inwardly and anteriorly at an angle of about 15° relative to the central axis C of cap 44. Anterior surface 46 of cap 44 includes three circumferentially spaced perimetrical notches 56 for receiving respective prongs 58 of a torque driving tool 60, as shown in FIG. 14. The exterior threads and diameter of side wall 48 are selected to threadingly mate with the interior threads of side wall 32 of screws holes 22 et seq.

Again referring to FIG. 11, the spherical undersurface of head 40 of bone screw 38 continues above the equator of head 40 to provide a spherical upper surface that is truncated by an end flat 62. A polygonal, or as preferred, Torx Plus 7 type recess 64 is provided in end flat 62 for receiving a torque driving tool, not shown. The spherical under and upper surfaces of head 40 of bone screw 38, as well as the frusto-conical surfaces 34 and 54 of screw holes 22 et seq. and locking cap 44, respectively, are grit blasted.

Figure 15:
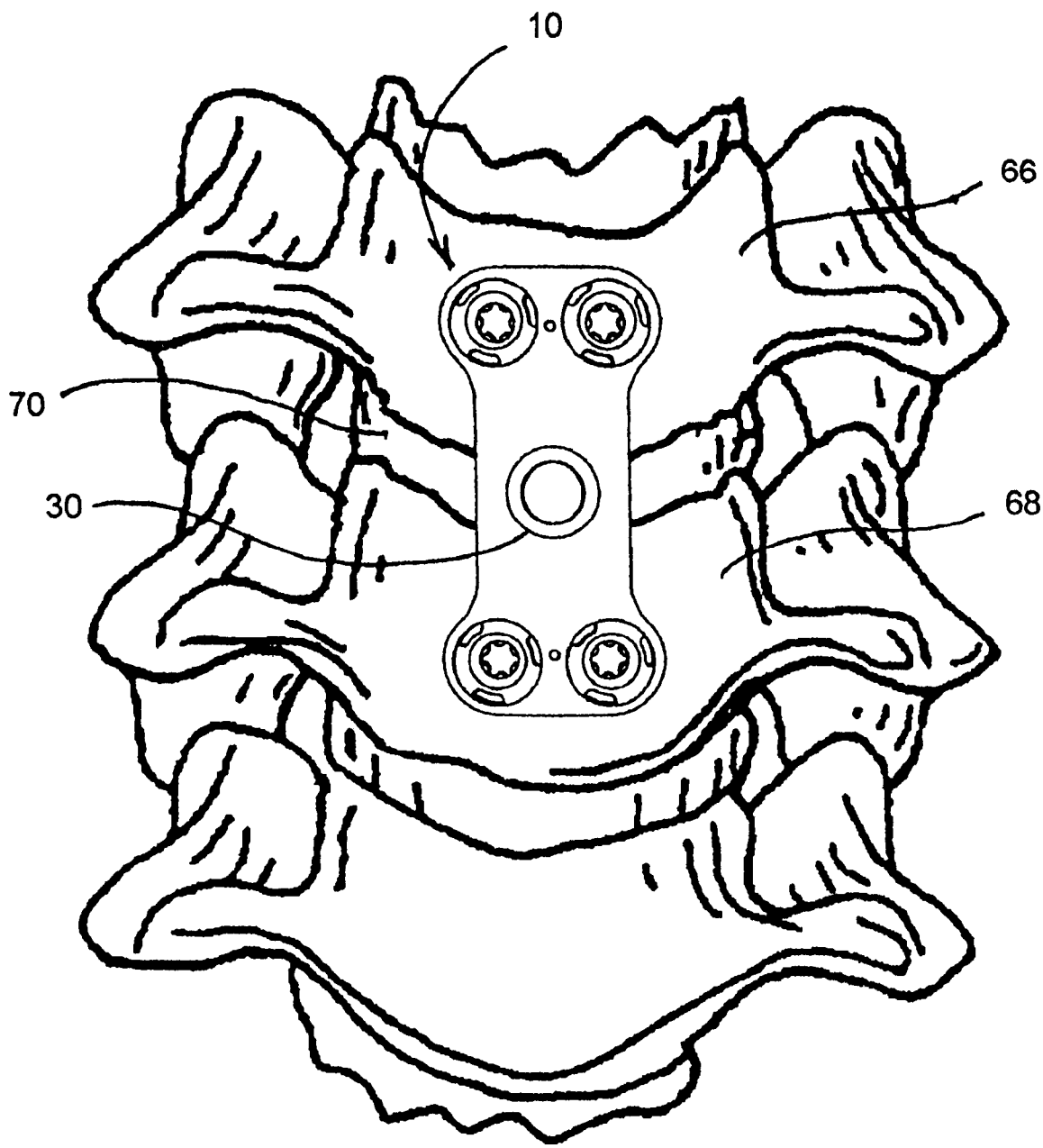
FIG. 15 is an anterior view of the plate, bone screws and locking caps of FIG. 7, affixed to a cervical vertebral column.
Figure 16:
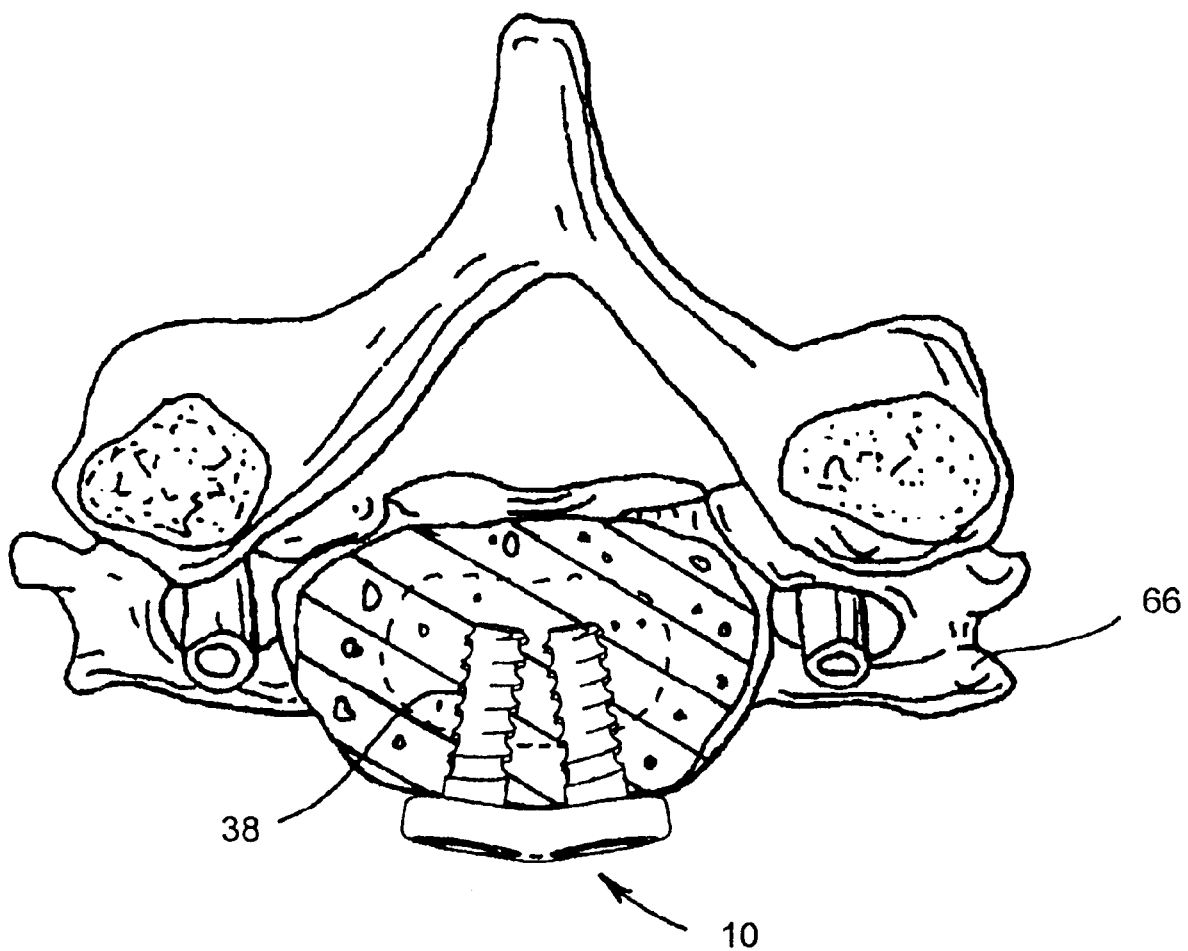
FIG. 16 is a superior view of the plate, bone screws and locking caps of FIG. 7 affixed to a cervical vertebrae that is shown partially in section.

The preferred manner of using the embodiment of the invention as described herein is as follows. The necessary surgical procedures are performed to gain access to the anterior surface of the cervical vertebral column at the location where the anterior cervical plating is to be implanted. The plate 10 is manipulated and placed in the desired location, as shown in FIG. 15 and 16, with the longitudinal axis L of plate 10 being oriented in the superior-inferior direction. The posterior, concave side of plate 10 is oriented toward the anterior surface of the cervical vertebrae 66 and 68. The location of the plate is adjusted to span two vertebrae. The screw holes 22 and 24 of end portion 18 overlie bone of one vertebrae 66, and the screw holes 26 and 28 of the other end portion 20 overlie bone of a next adjacent vertebrae 68. Screw hole 30 ovelies intervertebral disc 70. While holding plate 10 in the selected location, pilot holes are drilled through each of screw holes 22–28 and through the anterior cortical bone of the vertebrae in a direction selected by the surgeon. The direction of the axis of the pilot hole can vary up to 10° from the axis of the screw hole. Next, the bone screws are placed through the screw holes and driven into the pilot holes in the bone using a torque driver tool having a torx tip in driving engagement with the torx recess in the head of the bone screw. The bone screw is advanced into the bone until the head of the bone screw bottoms out against the frusto-conical side wall of the screw hole, whereupon the bone plate is drawn tight against the anterior surface of the cervical vertebrae. After all four bone screws are in place and tightened, each of the locking caps is placed over a respective bone screw head. Using a torque driver tool having a three prong tip in driving engagement with three recessed notches of the locking cap, the locking cap is screwed into place in the threaded screw holes. The locking cap is advanced until the frusto-conical wall on the posterior side of the locking cap engages the upper spherical surface of the bone screw. The locking cap captures the head of the bone screw under pressure between the frusto-conical side wall of the screw hole and the frusto-conical wall of the locking cap. Friction between the bone screw head, the screw hole and the locking cap holds the bone screw to the plate and prevents relative pivoting therebetween. The surface contact between the spherical and conical surfaces is substantially in the form of a circular line contact at the interfaces. Hole 52 of locking cap 44, being open at anterior surface 46, does not engage the end flat 62 of bone screw 38, to avoid inhibiting positioning of the axis of the threaded shank 42 of bone screw 38 at the desired angle.

Although the present invention has been illustrated and described in terms of a preferred embodiment, it should be understood that no limitation on the scope of the invention is intended thereby. The subject matter that is regarded as the invention is set forth in the claims that follow. Modifications and variations of the described embodiment will occur to persons skilled in the pertinent art. Any such modifications that fall within the appended claims are considered to be within the scope of the invention.

We claim:

1. An implantable device for affixing to the anterior side of cervical vertebrae for stablizing the cervical vertebral column, comprising:

a plate having an anterior surface and a posterior surface, said plate having a plurality of through holes, each said hole open at said anterior surface and at said posterior surface, each said hole having an anterior portion having a first diameter and a posterior portion having a second diameter smaller than said first diameter, said anterior portion of each said hole being internally threaded;

a bone screw having a threaded shank having a major diameter smaller than the second diameter of said through hole of said plate, and having a head having a major diameter greater than the second diameter of said through hole of said plate and smaller than the first diameter of said through hole of said plate; and a locking cap having an exterior thread and sized to be threadedly received within said anterior portion of said through hole of said plate while the head of the bone screw is disposed within said through hole for engaging and frictionally locking said head of said bone screw to said plate.

2. The implantable device of claim 1, in which said bone screw is sized relative to said through hole to permit polyaxial orientation of said bone screw relative to said plate.

3. The implantable device of claim 2, in which said bone screw has an undersurface that is subject to contact with said plate, said undersurface being substantially spherical.

4. The implantable device of claim 2, in which said bone screw has an upper surface that is subject to contact with said locking cap, said upper surface being substantially spherical.

5. The implantable device of claim 3, in which said plate has a portion subject to contact with said undersurface of said screw head, said plate portion being substantially conical.

6. The implantable device of claim 4, in which said locking cap has an undersurface that is subject to contact with said upper surface of said screw head, said undersurface of said locking cap being substantially conical.

7. The implantable device of claim 1, in which said bone screw has a surface that is subject to contact with said plate, said bone screw has a surface that is subject to contact with said locking cap, said plate has a surface subject to contact with said surface of said screw head, and said locking cap has a surface that is subject to contact with said surface of said screw head, at least one of said surfaces being grit blasted to increase friction upon contact.

8. The implantable device of claim 1, in which said head of said screw includes a polygonal recess for receiving a torque driver tool.

9. The implantable device of claim 1, in which said locking cap includes a recess for receiving a torque driver tool.

10. The implantable device of claim 9, in which said recess includes a plurality of perimetrical notches.

11. The implantable device of claim 1, in which said plate is pre-lordosed.

12. The implantable device of claim 1, in which said plate is curved to conform substantially to the anterior surface of the cervical vertebral column.

13. The implantable device of claim 1, in which said plate has a thickness not exceeding about 2.5 mm.

14. The implantable device of claim 1, in which said plate has a central portion having a thickness not exceeding about 2.0 mm.

15. The implantable device of claim 1, in which said plate has a central portion having a through hole.

\* \* \* \* \*